United States Patent [19]

Inoue

[11] Patent Number: 5,261,391
[45] Date of Patent: Nov. 16, 1993

[54] THREADED FLEXIBLE GUIDE TUBE FOR ENDOSCOPE

[75] Inventor: Masahiro Inoue, Tokyo, Japan

[73] Assignee: Kabushiki Kaisha Machida Seisakusho, Tokyo, Japan

[21] Appl. No.: 922,779

[22] Filed: Jul. 31, 1992

[30] Foreign Application Priority Data

Aug. 23, 1991 [JP] Japan ................. 3-237368

[51] Int. Cl.⁵ .............................. A61B 1/00
[52] U.S. Cl. ................................... 128/4
[58] Field of Search ............. 128/4, 6, 7, 8, 10, 128/11

[56] References Cited

U.S. PATENT DOCUMENTS

| | | |
|---|---|---|
| 3,960,143 | 6/1976 | Terada ..................... 128/4 |
| 4,419,987 | 12/1983 | Ogiu ........................ 128/4 |
| 4,771,766 | 9/1988 | Aoshiro et al. ............ 128/4 |
| 4,875,468 | 10/1989 | Krauter et al. . |
| 4,895,138 | 1/1990 | Yabe ........................ 128/6 |
| 4,928,699 | 5/1990 | Sasai ..................... 128/6 X |
| 4,967,732 | 11/1990 | Inoue . |
| 4,972,828 | 11/1990 | Ito .......................... 128/4 |

FOREIGN PATENT DOCUMENTS

| | | |
|---|---|---|
| 3111412 | 11/1982 | Fed. Rep. of Germany ......... 128/4 |
| 3621374 | 1/1987 | Fed. Rep. of Germany . |
| 3-15042 | 9/1986 | Japan . |

Primary Examiner—Richard J. Apley
Assistant Examiner—Karen A. Jalbert
Attorney, Agent, or Firm—Fish & Richardson

[57] ABSTRACT

There is disclosed an endoscope having a guide tube for guiding a forceps or the like. The guide tube connects an inlet port of a body to an outlet port of a tip member. A tubular connection portion extends rearwardly from a rear end face of the tip member. External threads are formed on an outer periphery of the connection portion. The inner diameter of the guide tube is greater than the inner diameter of the outlet port. Internal threads are formed on the inner periphery of the front end portion of the guide tube. The external threads on the connection portion are threadedly engaged with the internal threads on the guide tube to connect the front end portion of the guide tube to the outer periphery of the connection portion.

5 Claims, 2 Drawing Sheets

THREADED FLEXIBLE GUIDE TUBE FOR ENDOSCOPE

BACKGROUND OF THE INVENTION

This invention relates generally to an endoscope, and more particularly to an improved construction of connection between a tip member and a guide tube for guiding a forceps or the like.

Generally, an endoscope comprises a body, an insertion tube extending from the body, and a rigid tip member mounted on a distal end of the insertion tube. That portion of the insertion tube which is close to the tip member and has a predetermined length serves as a bending portion. This bending portion is bent in a remotely-manipulated manner by a manipulation means provided on the body. The endoscope further comprises a flexible guide tube for guiding a forceps and the like. The guide tube is connected at its proximal end to an inlet port in the body, and extends through the body and the insertion tube, and is connected at its distal end to an outlet port in the tip member.

A construction of connection between a tip member and a guide tube is shown in FIG. 3 of Japanese Utility Model Publication No. 3-15042. More specifically, a stepped bore is formed axially through the tip member. A front end portion of this stepped bore serves as an outlet port, and a rear end portion of the stepped bore is greater in diameter than the outlet port. A front end portion of a rigid connection pipe is press-fitted in the rear end portion of the stepped bore, and is fixedly secured thereto by soldering or the like. The rear end portion of this connection pipe is projected from the rear end face of the tip member, and the guide tube is mounted on the outer periphery of this connection pipe in an expanded manner.

In the above connection construction, even if an adhesive is provided between the connection pipe and the guide tube, the connection strength obtained is low. Furthermore, in the above connection construction, the inner diameter of the guide tube is equal to the diameter of the outlet port and the inner diameter of the connection pipe, and is relatively small. When the insertion tube is bent along a body cavity, or is bent by remote manipulation, the corresponding portion of the guide tube is also bent to have an oval cross-sectional shape. If the inner diameter of the guide tube is small, the resistance to the passage of a forceps is increased at that portion of the guide tube having such an oval cross-sectional shape.

An improved construction between a guide tube and a tip member is shown in FIG. 1 of the above Japanese Utility Model Publication No. 3-15042. More specifically, external threads are formed on the outer periphery of the front end portion of the guide tube. On the other hand, internal threads are formed on an inner periphery of a rear end portion of a stepped bore in the tip member. By threading the front end portion of the guide tube into the rear end portion of the stepped bore in the tip member, the guide tube and the tip member are connected together. In this connection construction, a high connection strength is obtained because of the use of the threaded connection. However, since the inner diameter of the guide tube is equal to the inner diameter of the outlet port, and is relatively small, the resistance to the passage of a forceps is increased at the bent portion of the guide tube, as described above. When it is intended to increase the inner diameter of the guide tube, the inner diameter of the rear end portion of the stepped bore must also be increased, and in this connection the diameter of the tip member must also be increased, because the strength of the tip member 1 is lowered if the inner diameter of the stepped bore is increased without increasing the outer diameter of the tip member.

SUMMARY OF THE INVENTION

It is an object of this invention to provide a construction of connection between a tip member and a guide tube in an endoscope, by which the strength of connection between the tip member and the guide tube can be increased, and the guide tube having a relatively large inner diameter can be used without increasing the outer diameter of the tip member.

According to the present invention, there is provided an endoscope comprising:

(a) a body having an inlet port;

(b) an insertion tube extending from the body;

(c) a rigid tip member mounted on a distal end of the insertion tube, the tip member having an outlet port;

(d) a flexible guide tube received in the body and the insertion tube to connect the inlet port of the body to the outlet port of the tip member, an inner diameter of the guide tube being greater than an inner diameter of the outlet port, and internal threads being formed on an inner periphery of a front end portion of the guide tube; and (e) a tubular connection portion extending from a rear end face of the tip member, the connection portion having a communication passage through which the outlet port is communicated with the guide tube, external threads being formed on an outer periphery of the connection portion, and the external threads being threadedly engaged with the internal threads on the guide tube to connect the front end portion of the guide tube to the outer periphery of the connection portion.

DESCRIPTION OF THE PREFERRED EMBODIMENTS

Figure 1:
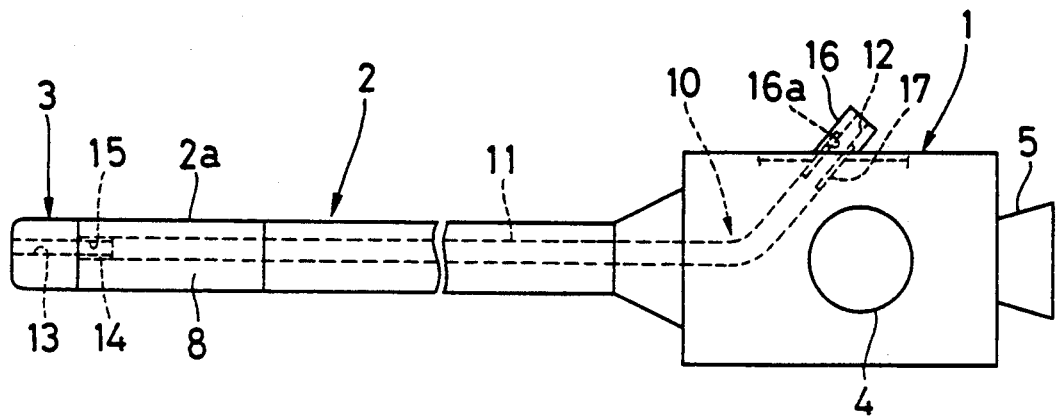
FIG. 1 is a front-elevational view of an endoscope according to the present invention.
Figure 2:
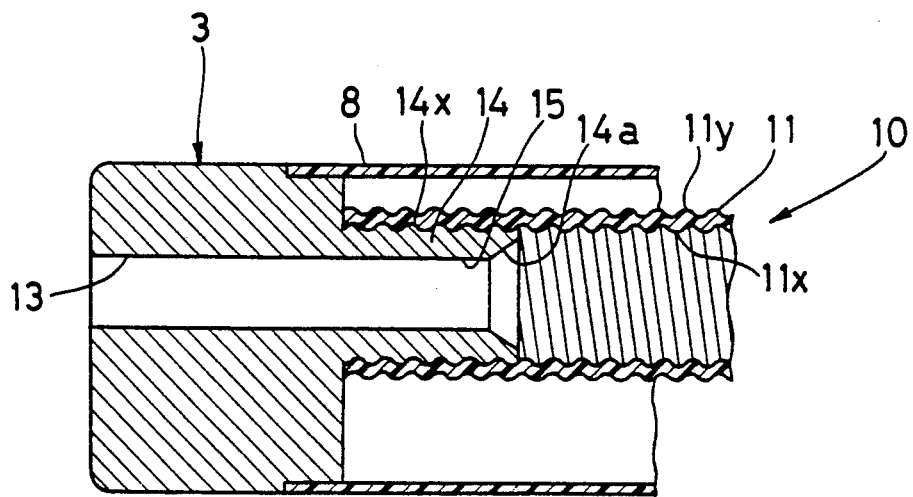
FIG. 2 is a cross-sectional view showing a construction of connection between a tip member and a guide tube in the endoscope.

The present invention will now be described with reference to the drawings. An endoscope comprises a body 1, a flexible insertion tube 2 extending from a front end of the body 1, and a rigid tip member 3 of metal or a rigid synthetic resin mounted on a front end of the insertion tube 2. An inspection window and an illumination window (both of which are not shown) are formed at a front end face of the tip member 3. That portion of the insertion tube 2 which is close to the tip member 3 and has a predetermined length serves as a bending portion 2a. The bending portion 2a is bent in a remotely-manipulated manner by a manipulation dial 4 mounted on the body 1. An ocular portion 5 is mounted on the body 1. The ocular portion 5 is connected to the inspection window of the tip member 3 via an optical system including an optical fiber, and with this arrangement a body cavity can be observed from the ocular portion 5. The illumination window is connected to a light source via an optical fiber bundle which passes through the insertion tube 2, the body 1 and a cable (not shown) connected to the body 1. With this arrangement, light from the light source is supplied into the body cavity through the illumination window. The construction of the insertion tube 2 including the bending portion 2a is well known in the art, and therefore will not be explained here, and only a protective tube 8 of a soft synthetic resin at an outermost layer of the insertion tube 2 is shown in the drawings. As shown in FIG. 2, the front end of the protective tube 8 is mounted on the outer periphery of the rear end portion of the tip member 3.

The endoscope includes a guide means 10 for guiding a long forceps. The guide means 10 includes a flexible guide tube 11 of a soft synthetic resin, an inlet port 12 formed at the body 1, and an outlet port 13 formed at the tip member 3. The inner diameter of the guide tube 11 is greater than the inner diameter of the inlet port 12 and the inner diameter of the outlet port 13. The proximal end of the guide tube 11 is connected to the inlet port 12 in the body 1. The guide tube 11 extends through the body 1 and the insertion tube 2, and is connected at its distal end to the outlet port 13 in the tip member 3.

The construction of connection between the guide tube 11 and the tip member 3 will now be described. The outlet port 13 is formed in and extends axially through the tip member 3. A tubular connection portion 14 is formed integrally with the tip member 3, and extends rearwardly from the rear end face of the tip member 3, the connection portion 14 being coaxial with the outlet port 13. The connection portion 14 has a communication passage 15 communicated with the outlet port 13. The diameter of the outlet port 13 is equal to the diameter of the communication passage 15. A tapered portion 14a is formed at the rear end of the communication passage 15. External threads 14x are formed on the outer periphery of the connection portion 14. The guide tube 11 has a uniform diameter throughout the length thereof. The guide tube 11 is in the form of a bellows having a uniform thickness throughout the length thereof, and has internal threads 11x at its inner periphery and external threads 11y at its outer periphery. The front or distal end portion of the guide tube 11 is connected to the outer periphery of the connection portion 14 by threadedly engaging the internal threads 11x of the guide tube 11 with the external threads 14x of the connection portion 14.

Next, the construction of connection between the guide tube 11 and the body 1 will now be described. The body 1 has a projection 16 projected outwardly therefrom, and a stepped bore 16a is formed in the projection 16. An outer end portion of the stepped bore 16a serves as the above-mentioned inlet port 12. An inner end portion of the stepped bore 16a is greater in diameter than the inlet port 12. The proximal end portion of the guide tube 11 is connected to the inner end portion of the stepped bore 16a through a connection tube 17 of metal or a rigid synthetic resin. More specifically, the connection tube 17 has external threads on the outer periphery of one end portion thereof, and the proximal end portion of the guide tube 11 is threadedly connected to this externally-threaded portion of the connection tube 17. The other end portion of the connection tube 17 is inserted into the inner end portion of the stepped bore 16a, and is fixedly secured to the body 1 by soldering or the like.

In the above construction, the guide means 10 guides the long forceps which has a flesh-collecting portion at its distal end, and a manipulation portion at its proximal end for remotely manipulating the collecting portion. More specifically, the forceps is inserted from the inlet port 12 into the guide tube 11, and is guided by the guide tube 11, so that the distal end of the forceps is projected from the outlet port 13 to face a body cavity. A piece of flesh on the inner wall of the body cavity is collected by remotely manipulating the collecting portion of the forceps.

In the above construction of connection between the guide tube 11 and the tip member 3, since the distal end portion of the guide tube 11 is threadedly connected to the outer periphery of the connection portion 14, the strength of connection between the two can be enhanced.

The inner diameter of the guide tube 11 is larger than the diameter of the outlet port 13, and therefore for example, when the bending portion 2a is bent, so that the corresponding portion of the guide tube 11 is deformed into an oval cross-sectional shape, this deformed portion will not prevent the passage of the forceps, and the resistance to the passage of the forceps is small. Speaking from a different aspect, even if the inner diameter of the guide tube 11 is increased, the diameter of the output port 13 can be kept small, and the outer diameter of the tip member 13 does not need to be increased. Incidentally, if the outer diameter of the tip member 3 is increased, this gives a greater pain to the patient.

The collecting portion at the distal end of the forceps is guided by the tapered portion 14a of the connection portion 14, and therefore can be smoothly introduced from the guide tube 11 into the communication passage 15 of a smaller diameter.

Figure 3:
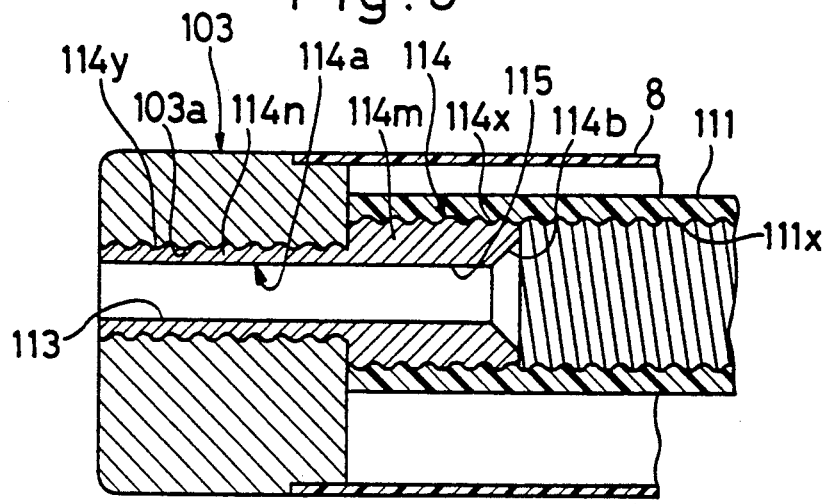
FIGS. 3 to 5 are views showing modified connection constructions, respectively.
Figure 4:
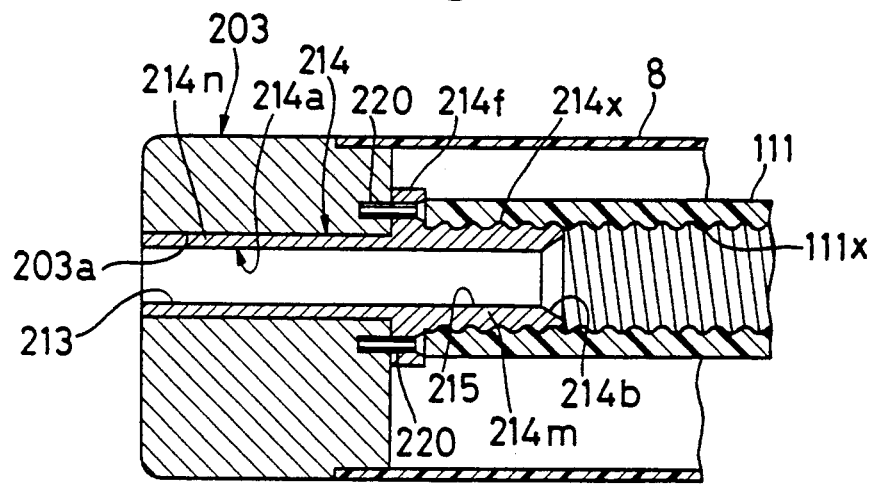
Figure 5:
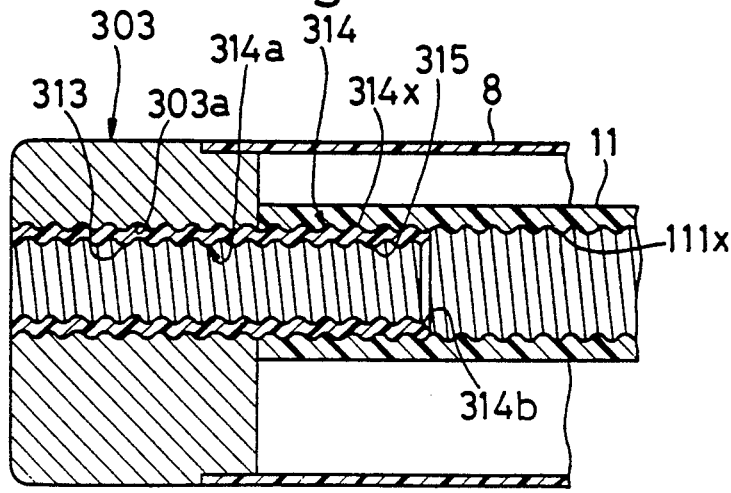

FIGS. 3 to 5 show other preferred embodiments of the present invention, respectively. Those portions of these embodiments corresponding to those of the preceding embodiment are designated by identical reference numerals, respectively, and detailed explanation thereof will be omitted.

In the embodiment shown in FIG. 3, a mounting hole 103a in the form of a threaded hole is formed axially through a tip member 103. There is provided a connection pipe or tube 114 separate from the tip member 103. The connection pipe 114 has a through hole (internal bore) 114a. A front end portion of the through hole 114a serves as an outlet port 113, and a rear end portion thereof serves as a communication passage 115. A tapered portion 114b is formed at the rear end of the through hole 114a. The connection pipe 114 has a larger-diameter rear portion (connection portion) 114m, and a smaller-diameter front portion 114n. External threads 114x are formed on the outer periphery of the larger-diameter portion 114m, and external threads 114y are formed on the outer periphery of the smaller-diameter portion 114n. The smaller-diameter portion 114n of the connection pipe 114 is threaded into the mounting hole 103a of the tip member 103 until the front end face of the larger-diameter portion 114m is brought into contact with the rear end face of the tip member 103. By doing so, the connection pipe 114 is connected to the tip member 103. A guide tube 111 used in this embodiment has a uniform diameter throughout a length thereof, and has internal threads 111x on its inner periphery, and has a cylindrical outer peripheral surface. The guide tube 111 is threadedly connected to the outer periphery of the larger-diameter portion 114m of the connection pipe 114.

In the embodiment shown in FIG. 4, a mounting hole 203a is formed axially through a tip member 203. A connection pipe 214 separate from the tip member 203 has a through hole (internal bore) 214a, and also has a larger-diameter rear portion (connection portion) 214m, a smaller-diameter front portion 214n, and a flange 214f between the two portions 214m and 214n. A front end portion of the through hole 214a serves as an outlet port 213, and a rear end portion thereof serves as a communication passage 215. A tapered portion 214b is formed at the rear end of the through hole 214a. The outer diameter of the smaller-diameter portion 214n is equal to the inner diameter of the mounting hole 203a. The smaller-diameter portion 214n of the connection pipe 214 is inserted into the mounting hole 203a in the tip member 203, with the flange 214f held against the rear end face of the tip member 203, and in this condition bolts 220 are threaded into the rear end face of the tip member 203 through the flange 214f, thereby fixedly securing the connection pipe 214 to the tip member 203. External threads 214x are formed on the outer periphery of the lager-diameter portion 214m. A guide tube 111 is threadedly connected to the outer periphery of the larger-diameter portion 214m.

In the embodiment shown in FIG. 5, a mounting hole 303a in the form of a threaded hole is formed axially through a tip member 303. A connection pipe 314 separate from the tip member 303 is in the form of a threaded pipe whose outer diameter is uniform throughout the length thereof, the threaded pipe having external threads 314x over the entire outer peripheral surface thereof. The connection pipe 314 is fixedly secured to the tip member 303 by threading the front end portion of the connection pipe 314 into the mounting hole 303a. A guide tube 111 is threadedly connected to the rear end portion (connection portion) of the connection pipe 314 projected from the rear end face of the tip member 303. A front end portion of a through hole 314a in the connection pipe 314 serves as an outlet port 313, and a rear end portion of thereof serves as a communication passage 315. A tapered portion 314b is formed at rear end of the through hole 314a.

The present invention is not limited to the above embodiments, and suitable modifications can be made without departing the scope of the invention. For example, the present invention can be applied to a construction of connection between a tip member and a guide tube for guiding an elongate member having a brush at its distal end, or for guiding the air, water or the like. The outlet port may be open to the outer peripheral surface of the tip member. Internal threads may be formed only on the inner periphery of the front end portion of the guide tube. For connecting the connection pipe and the tip member together and for connecting the guide tube and the connection portion together, an adhesive may be used.

What is claimed is:

1. An endoscope comprising:
   (a) a body having an inlet port;
   (b) an insertion tube extending from said body;
   (c) a rigid tip member mounted on a distal end of said insertion tube, said tip member having an outlet port;
   (d) a flexible guide tube received in said body and said insertion tube to connect said inlet port of said body to said outlet port of said tip member, an inner diameter of said guide tube being greater than an inner diameter of said outlet port, and internal threads being formed on an inner periphery of a front end portion of said guide tube; and
   (e) a tubular connection portion extending from a rear end face of said tip member, said connection portion having a communication passage through which said outlet port is communicated with said guide tube, external threads being formed on an outer periphery of said connection portion, and said external threads being threadedly engaged with said internal threads on said guide tube to connect the front end portion of said guide tube to the outer periphery of said connection portion, said endoscope further comprising a connection pipe which is separate form said tip member and has a through hole, said tip member having a mounting hole, said connection pipe being fixed to said tip member in such a manner that a front end portion of said connection pipe is inserted in said mounting hole in said tip member, a rear end portion of said connection pipe being projected from the rear end face of said tip member to serve as said connection portion for connecting said guide tube thereto, and at least a rear end portion of said through hole serving as said communication passage, and wherein the rear end portion of said connection pipe serving as said connection portion for said guide tube is greater in diameter than the front end portion of said connection pipe inserted in said mounting hole in said tip member.

2. An endoscope according to claim 1, in which a tapered portion is formed at a rear end of said communication passage in said connection portion.

3. An endoscope comprising:
   (a) a body having an inlet port;
   (b) an insertion tube extending from said body;
   (c) a rigid tip member mounted on a distal end of said insertion tube, said tip member having an outlet port;
   (d) a flexible guide tube received in said body and said insertion tube to connect said inlet port of said body to said outlet port of said tip member, an inner diameter of said guide tube being greater than an inner diameter of said outlet port, and internal threads being formed on an inner periphery of a front end portion of said guide tube; and
   (e) a tubular connection portion extending from a rear end face of said tip member, said connection portion having a communication passage through which said outlet port is communicated with said guide tube, external threads being formed on an outer periphery of said connection portion, and said external threads being threadedly engaged with said internal threads on said guide tube to connect the front end portion of said guide tube to the outer periphery of said connection portion, said endoscope further comprising a connection pipe which is separate from said tip member and has a through hole, said tip member having a mounting hole, said connection pipe being fixed to said tip member in such a manner that a front end portion of said connection pipe is inserted in said mounting hole in said tip member, a rear end portion of said connection pipe being projected from the rear end face of said tip member to serve as said connection portion for connecting said guide tube thereto, and at least a rear end portion of said through hole serving as said communication passage, and wherein said connection pipe has a flange formed on an outer periphery thereof intermediate opposite ends thereof, said flange being mated with and fixedly secured to the rear end face of said tip member by bolts threaded into the rear end face of said tip member through said flange, thereby fixing said connection pipe to said tip member.

4. An endoscope according to claim 3, in which a front end portion of said through hole in said connection pipe serves as said outlet port.

5. An endoscope comprising:
    (a) a body having an inlet port;
    (b) an insertion tube extending from said body;
    (c) a rigid tip member mounted on a distal end of said insertion tube, said tip member having an outlet port;
    (d) a flexible guide tube received in said body and said insertion tube to connect said inlet port of said body to said outlet port of said tip member, an inner diameter of said guide tube being greater than an inner diameter of said outlet port, and internal threads being formed on an inner periphery of a front end portion of said guide tube; and
    (e) a tubular connection portion extending from a rear end face of said tip member, said connection portion having a communication passage through which said outlet port is communicated with said guide tube, external threads being formed on an outer periphery of said connection portion, and said external threads being threadedly engaged with said internal threads on said guide tube to connect the front end portion of said guide tube to the outer periphery of said connection portion, said endoscope further comprising:

a connection pipe which is separate from said tip member and has a through hole, said tip member having a mounting hole, said connection pipe being fixed to said tip member in such a manner that a front end portion of said connection pipe is inserted in said mounting hole in said tip member, a rear end portion of said connection pipe being projected from the rear end face of said tip member to serve as said connection portion for connecting said guide tube thereto, and at least a rear end portion of said through hole serving as said communication passage, and wherein said mounting hole in said tip member is in the form of a threaded hole, said connection pipe has said external threads over the entire outer peripheral surface, an outer diameter of said connection pipe is uniform throughout the length thereof, a front end portion of said connection pipe is threaded into said mounting hole, and said rear end portion of said connection pipe is threaded into said front end portion of said guide tube.

* * * * *